United States Patent
Triki

(10) Patent No.: US 9,833,189 B2
(45) Date of Patent: Dec. 5, 2017

(54) SLEEP APNEA DIAGNOSIS SYSTEM AND METHOD OF GENERATING INFORMATION USING NON-OBTRUSIVE AUDIO ANALYSIS

(71) Applicant: KONINKLIJKE PHILIPS N.V., Eindhoven (NL)

(72) Inventor: Mahd Triki, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 245 days.

(21) Appl. No.: 14/647,475

(22) PCT Filed: Dec. 16, 2013

(86) PCT No.: PCT/IB2013/060983
§ 371 (c)(1),
(2) Date: May 27, 2015

(87) PCT Pub. No.: WO2014/097114
PCT Pub. Date: Jun. 26, 2014

(65) Prior Publication Data
US 2015/0297131 A1    Oct. 22, 2015

Related U.S. Application Data

(60) Provisional application No. 61/738,026, filed on Dec. 17, 2012.

(51) Int. Cl.
*A61B 5/08* (2006.01)
*A61B 5/00* (2006.01)
(Continued)

(52) U.S. Cl.
CPC ............ *A61B 5/4818* (2013.01); *A61B 5/087* (2013.01); *A61B 5/11* (2013.01); *A61B 5/7207* (2013.01);
(Continued)

(58) Field of Classification Search
CPC ......... A61B 5/4818; A61B 5/087; A61B 5/11; A61B 5/7207; A61B 7/003;
(Continued)

(56) References Cited

U.S. PATENT DOCUMENTS 4,802,485 A   2/1989   Bowers et al.
5,797,852 A   8/1998   Karakasoglu et al.
(Continued)

FOREIGN PATENT DOCUMENTS

EP    1410759 A1    4/2004
WO    2007071812 A1    6/2007
(Continued)

OTHER PUBLICATIONS

Yu, Shiann-Jeng, and Ju-Hong Lee. "Adaptive array beamforming based on an efficient technique." IEEE Transactions on Antennas and Propagation 44.8 (1996): 1094-1101.*
(Continued)

*Primary Examiner* — Christian Jang
*Assistant Examiner* — Andrey Shostak

(57) ABSTRACT

An electronic apparatus includes an array of microphones for detecting audible sounds generated by a patient and for generating audio information representing the detected audible sounds, a first beamformer having a first adaptability speed and configured to generate first audio information and first noise information from the audio information, a second beamformer having a second adaptability speed which is slower than the first adaptability speed, the second adaptive beamformer configured to generate second audio information and second noise information from the audio information, an audio classification unit for generating audio classification information based on the first audio information, a head movement detection unit for generating head movement information based on at least one of the second audio
(Continued)

information, the first noise information, and the second noise information, and a diagnosis unit for determining a sleep apnea diagnosis based on the audio classification information and the head movement information.

15 Claims, 3 Drawing Sheets

(51) Int. Cl.
A61B 7/00 (2006.01)
A61B 5/11 (2006.01)
H04R 3/00 (2006.01)
A61B 5/087 (2006.01)
H04R 1/08 (2006.01)
H04R 1/40 (2006.01)

(52) U.S. Cl.
CPC ............... *A61B 7/003* (2013.01); *H04R 1/08* (2013.01); *H04R 3/005* (2013.01); *A61B 2562/04* (2013.01); *H04R 1/406* (2013.01); *H04R 2410/01* (2013.01); *H04R 2430/23* (2013.01)

(58) Field of Classification Search
CPC ...... A61B 2562/04; H04R 1/08; H04R 1/406; H04R 3/005; H04R 2430/23; H04R 2410/01
See application file for complete search history.

(56) References Cited

U.S. PATENT DOCUMENTS

| 6,241,683 | B1* | 6/2001 | Macklem ............... A61B 5/091 600/529 |
| 6,811,538 | B2 | 11/2004 | Westbrook et al. |
| 7,559,903 | B2 | 7/2009 | Moussavi et al. |
| 2009/0164212 | A1 | 6/2009 | Chan et al. |
| 2010/0014690 | A1* | 1/2010 | Wolff ..................... H04R 3/005 381/92 |
| 2011/0087079 | A1* | 4/2011 | Aarts ..................... A61B 7/003 600/300 |
| 2012/0099732 | A1* | 4/2012 | Visser ................. G10L 21/0272 381/17 |
| 2013/0289432 | A1* | 10/2013 | Van Vugt ............. A61B 5/0077 600/534 |
| 2013/0310657 | A1* | 11/2013 | Sullivan ............... A61B 5/6892 600/301 |

FOREIGN PATENT DOCUMENTS

| WO | 2009034524 A1 | 3/2009 |
| WO | 2011015979 A2 | 2/2011 |
| WO | 2011141916 A1 | 11/2011 |
| WO | 2011150362 A2 | 12/2011 |

OTHER PUBLICATIONS

Watermark Medical, http://www.watermarkmedical.com/products.php, Downloaded May 15, 2015, 2 Pages.
IM Systems, http://www.imsystems.net/sleepcheck/sleepcheck_sos.htm, Downloaded May 15, 2015, 1 Page.
The Sleep Wellness Institute, http://www.sleepwellandlive.com/, Downloaded May 15, 2015, 2 Pages.
Danbury Hosptial, http://www.danburyhospital.org/en/our-services/care, Downloaded May 15, 2015, 2 Pages.
Yadollahi, "Apnea Detection by Acoustical Means", Proceedings of the 28th IEEE, EMBS Annual International Conference, 2006, pp. 4623-4626.
Ng et al, "Using Psychoacoustics of Snoring Sounds to Screen for Obstructive Sleep Apnea", Engineering in Medicine and Biology Society, 2008, pp. 1647-1650.
Karci et al, "Detection of Post Apnea Sounds and Apnea Periods From Sleep Sounds", Engineering in Medicine and Biology Society, 2011, pp. 6075-6078.

* cited by examiner

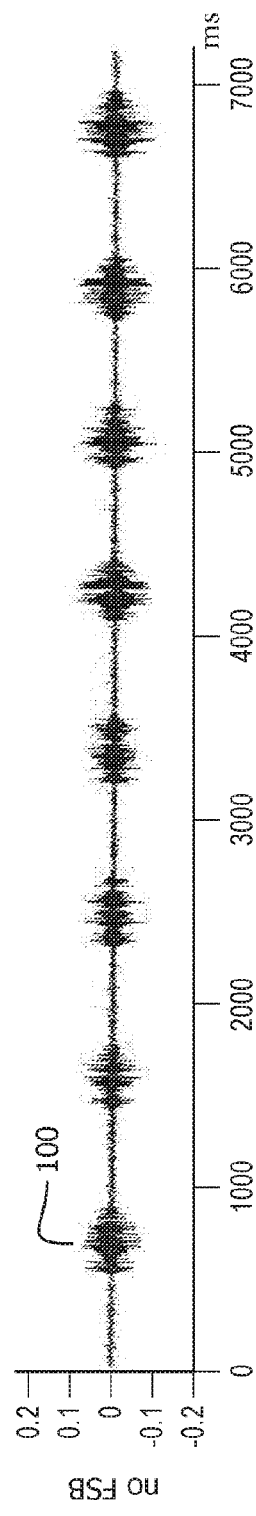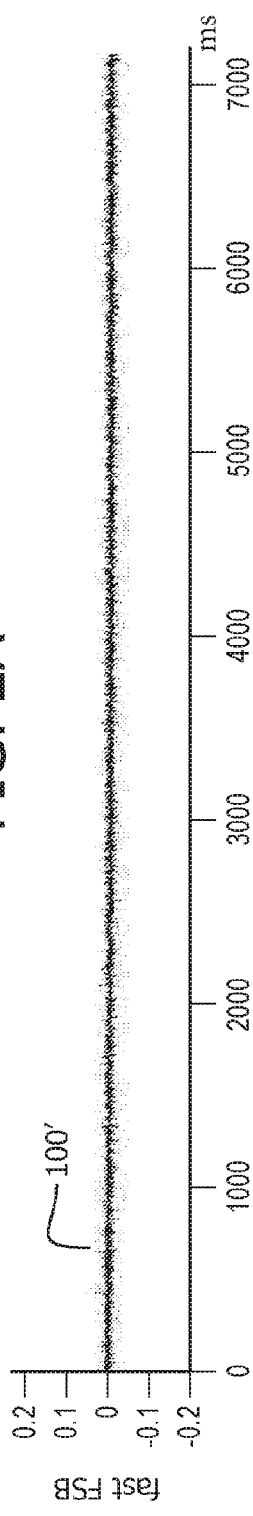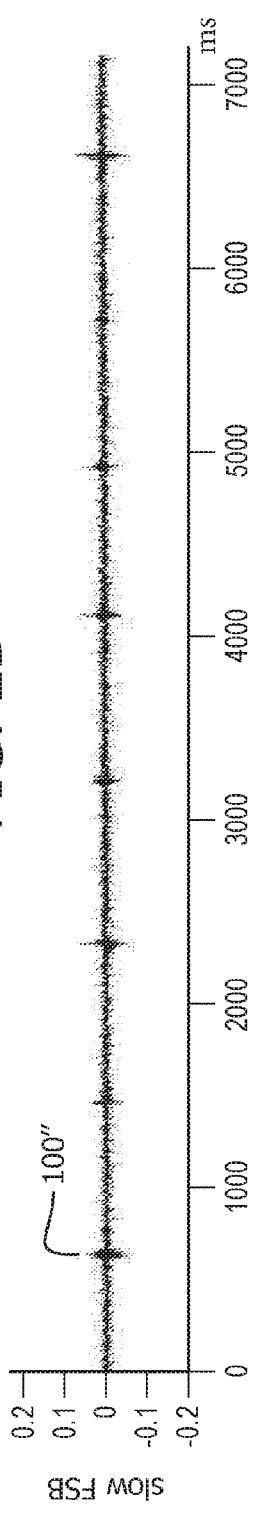

SLEEP APNEA DIAGNOSIS SYSTEM AND METHOD OF GENERATING INFORMATION USING NON-OBTRUSIVE AUDIO ANALYSIS

CROSS-REFERENCE TO PRIOR APPLICATIONS

This application is the U.S. National Phase application under 35 U.S.C. §371 of International Application Serial No. PCT/IB2013/060983, filed on Dec. 16, 2013, which claims the benefit of U.S. application Ser. No. 61/738,026, filed on Dec. 17, 2012. These applications are hereby incorporated by reference herein.

BACKGROUND OF THE INVENTION

1. Field of the Invention

The present invention pertains to sleep apnea diagnosis, and, in particular, to a sleep apnea diagnosis system and method.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Various methods have been used to assess whether a patient suffers from OSA. The most comprehensive method is a clinical polysomnogram (PSG), which can diagnose many significant sleep pathologies. However, a PSG requires special hospital or sleep disorder center over-night stays with technicians present to monitor both the equipment and the patient.

Home use devices which measure and combine blood oxygen saturation, pulse rate, airflow, snoring level and head movements have also been used to assess sleep apnea. While these devices are less expensive than a PSG, the devices are still too expensive and obtrusive.

Questionnaires and tests have also been used to assess sleep apnea. However, although questionnaires and tests are cost-free and easy to take, their accuracy in assessing sleep apnea is very limited.

Audio recording has also been used to assess sleep apnea. While audio recording can be accomplished inexpensively and non-obtrusively, the audio recording is sensitive to noise such as ambient noise, a snoring partner, or other noises, thus reducing the accuracy of the technique.

Accordingly, a need exists for improvement in assessing sleep apnea and, for example, for an inexpensive and non-obtrusive way to accurately assess sleep apnea.

SUMMARY OF THE INVENTION

In one embodiment, an electronic apparatus is provided and includes an array of microphones for detecting audible sounds generated by a patient and for generating audio information representing the detected audible sounds generated by the patient, a first beamformer having a first adaptability speed and configured to generate first audio information and first noise information from the audio information, a second beamformer having a second adaptability speed which is slower than the first adaptability speed, the second adaptive beamformer configured to generate second audio information and second noise information from the audio information, an audio classification unit for generating audio classification information based on the first audio information, a head movement detection unit for generating head movement information based on at least one of the second audio information, the first noise information, and the second noise information, and a diagnosis unit for determining a sleep apnea diagnosis based on the audio classification information and the head movement information.

In another embodiment, a method of generating audio classification information and head movement information is provided which includes detecting audible sounds generated by a patient with an array of microphones and generating audio information representing the detected audible sounds generated by the patient, processing the audio information with a first beamformer having a first adaptability speed and generating first audio information and first noise information from the audio information, processing the audio information with a second beamformer having a second adaptability speed which is slower than the first adaptability speed and generating second audio information and second noise information from the audio information, generating audio classification information based on the first audio information, and generating head movement information based on at least one of the second audio information, the first noise information, and the second noise information.

In another embodiment, a non-transitory computer readable medium storing one or more programs, including instructions, which when executed by a computer, causes the computer to perform a method is provided. The method includes detecting audible sounds generated by a patient with an array of microphones and generating audio information representing the detected audible sounds generated by the patient, processing the audio information with a first beamformer having a first adaptability speed and generating first audio information and first noise information from the audio information, processing the audio information with a second beamformer having a second adaptability speed which is slower than the first adaptability speed and generating second audio information and second noise information from the audio information, generating audio classification information based on the first audio information, generating head movement information based on at least one of the second audio information, the first noise information, and the second noise information, and determining a sleep apnea diagnosis based on the audio classification information and the head movement information.

BRIEF DESCRIPTION OF THE DRAWINGS

FIG. 2A is a graph of exemplary audio information of a patient;

FIG. 2B is a graph of exemplary noise information output from a fast beamformer;

FIG. 2C is a graph of exemplary noise information output from a slow beamformer.

DETAILED DESCRIPTION OF EXEMPLARY EMBODIMENTS

Figure 1:
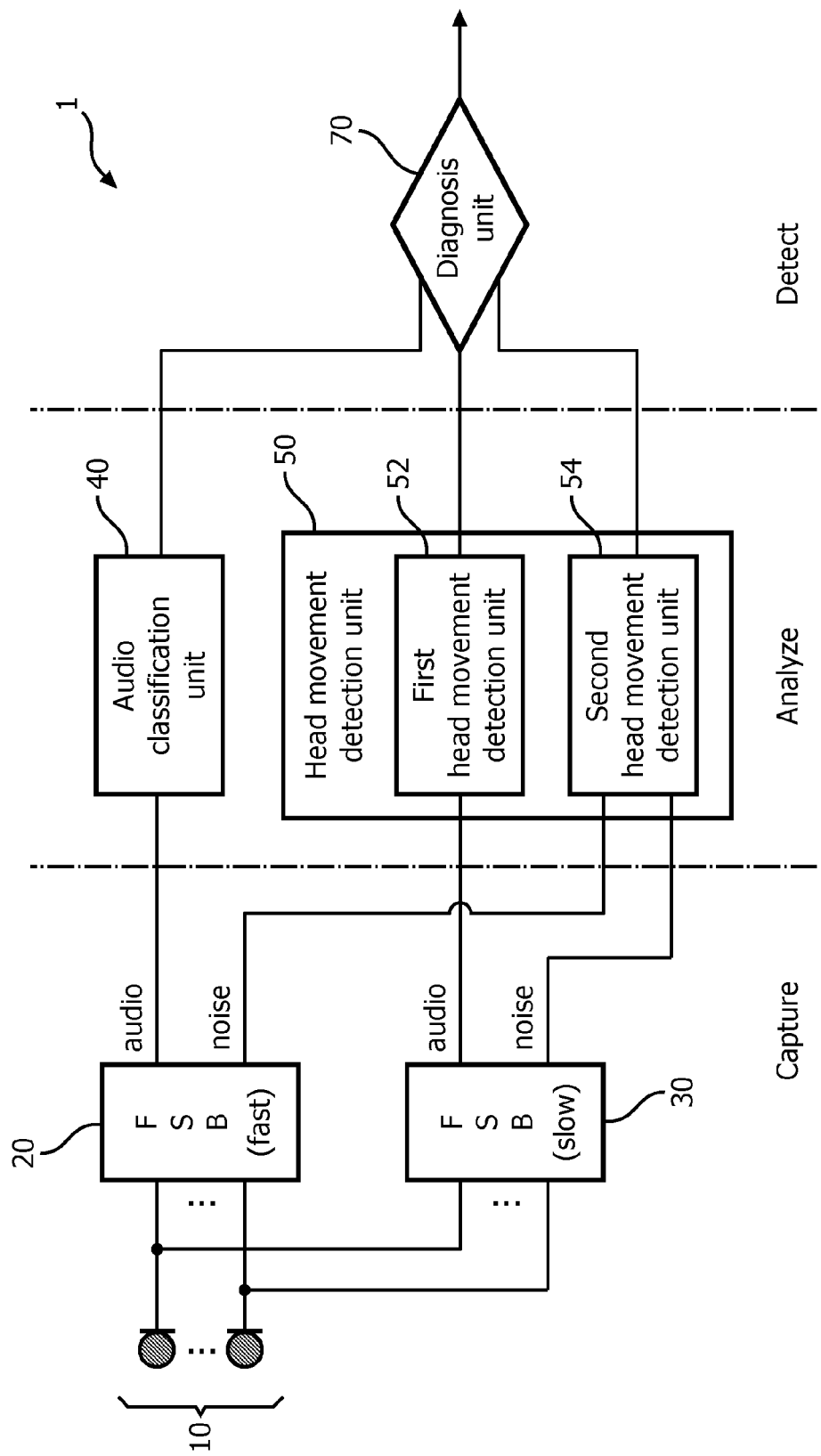
FIG. 1 is a diagram of a sleep apnea diagnosis system according to one exemplary embodiment.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the phrase "adaptability speed of a beamformer" shall mean a speed at which a beamformer can converge on a new target location.

FIG. 1 is a block diagram of a system 1 adapted to diagnose sleep apnea according to one exemplary embodiment of the present disclosed concept. System 1 is configured to record audible sounds generated by a patient, and through the recorded sounds, to detect snoring of the patient and head movement of the patient. System 1 analyzes the snoring and head movement patterns to assess sleep apnea of the patient.

System 1 includes an array of microphones 10. Array of microphones 10 are operable to record the audible sounds generated by the patient. In the exemplary embodiment shown in FIG. 1, array of microphones 10 includes multiple microphones. One skilled in the art will understand that any number of microphones greater than one can be utilized without deviating from the scope of the present disclosed concept. Increasing the number of microphones in array of microphones 10 allows a narrower beam to be formed by array of microphones 10.

In some exemplary embodiments, array of microphones 10 are arranged as a linear array of microphones. In some other exemplary embodiments, array of microphones are arranged in a symmetric shape (e.g., without limitation, triangular, rectangular, etc.). The symmetric shape can deliver consistent performance when an orientation of array of microphones 10 with respect to the patient is not previously known. In some exemplary embodiments, array of microphones 10 are arranged within about 10 cm of each other. However, the present disclosed concept is not limited thereto. Array of microphones 10 may be arranged in any suitable manner without departing from the scope of the present disclosed concept.

System 1 also includes fast beamformer 20 and slow beamformer 30. Each of fast beamformer 20 and slow beamformer 30 receive and process outputs of each microphone in array of microphones 10. Fast beamformer 20 and slow beamformer 30 process the outputs of each microphone in array of microphones 10 so as to each form a directional beam such that sounds received from directions inside the beam are enhanced while sounds received from directions outside the beam are attenuated.

Fast beamformer 20 and slow beamformer 30 focus the direction of their beams on the patient's head and adapt the direction of their beams based on movements of the patient's head. For example and without limitation, fast beamformer 20 and slow beamformer 30 can use the patient's snoring to determine the direction of the patient's head and track the patient's head. However, the fast beamformer 20 and the slow beamformer 30 do not adapt to the direction of the patient's head at the same speed. Rather, fast beamformer 20 has an adaptability speed that is faster than an adaptability speed of slow beamformer 30. In an exemplary embodiment, fast beamformer 20 has an adaptability speed that is fast enough to track normal movements of the patient (e.g., without limitation, movement of the head due to snoring), whereas slow beamformer 30 has an adaptability speed that is not fast enough to track normal head movements of the patient, but is fast enough to track normal body movements of the patient (e.g., without limitation, shifting body position during sleeping). As such, during periods of patient head movement, which is common during snoring events, the beam of fast beamformer 20 remains focused on the patient's head while the beam of slow beamformer 30 is not precisely focused on the patient's head.

In a further exemplary embodiment, fast beamformer 20 has an adaptability speed of less than one second and slow beamformer 30 has an adaptability speed of greater than ten seconds. It is understood that an adaptability speed of less than one second is fast enough to track normal head movement speed and an adaptability speed of greater than ten seconds is not fast enough to track normal head movements, but is fast enough to track normal body movement.

Fast beamformer 20 and slow beamformer 30 may each be any suitable type of beamformer. In the exemplary embodiment shown in FIG. 1, fast beamformer 20 and slow beamformer 30 are filter and sum type beamformers. In other embodiments, fast beamformer 20 and slow beamformer 30 can be implemented as delay and sum type beamformers.

Fast beamformer 20 and slow beamformer 30 each output enhanced audio information and noise information. The enhanced audio information is information of sounds which are located inside the beams of fast beamformer 20 and slow beamformer 30. The noise information is information of sounds which are located outside the beams of fast beamformer 20 and slow beamformer 30.

FIGS. 2A, 2B, and 2C illustrate exemplary inputs to fast beamformer 20 and slow beamformer 30 along with some outputs from fast beamformer 20 and slow beamformer 30. Referring first to FIG. 2A, exemplary audio information output from array of microphones 10 during periods of snoring and head movement of a patient is illustrated. As shown in FIG. 2A, a snoring event 100 causes a rise in the amplitude of the signal.

Referring now to FIG. 2B, an exemplary noise reference output of fast beamformer 20 is shown. As described above, the noise information output from fast beamformer 20 only includes audio information from directions located outside the beam. Since the beam of fast beamformer 20 is focused on the patient's head, the snoring event 100' in the noise information does not rise in amplitude. Rather, as shown in FIG. 2B, the noise information output from fast beamformer 20 only includes ambient noise.

Referring now to FIG. 2C, an exemplary noise information output of slow beamformer 30 is shown. As described above, slow beamformer 30 does not adapt fast enough to precisely track movements of the patient's head. As such, during snoring event 100" some of the snoring audio will remain in the noise information output from the slow beamformer 30. The difference between the noise information of fast beamformer 20 and slow beamformer 30 indicates that patient head movement is also present during snoring event 100.

While FIGS. 2B and 2C illustrate exemplary noise information output from fast beamformer 20 and slow beamformer 30, fast beamformer 20 and slow beamformer 30 also output enhanced audio information. As described above, the enhanced audio information is audio information from directions inside the beams of fast beamformer 20 and slow beamformer 30. During periods of snoring and head movement of the patient, the enhanced audio information output from fast beamformer 20 and slow beamformer 30 will differ as slow beamformer 30 is not able to keep its beam focused on the patient's head during periods of head movement.

Referring again to FIG. 1, outputs of the fast beamformer 20 and slow beamformer 30 are output to an audio classification unit 40 and a head movement detection unit 50 which includes a first head movement detection unit 52 and a second head movement detection unit 54. In the exemplary embodiment shown in FIG. 1, the enhanced audio information from fast beamformer 20 is output to audio classification unit 40 and the enhanced audio information from slow beamformer 30 is output to first head movement detection unit 52. The noise information from both fast beamformer 20 and slow beamformer 30 is output to second head movement detection unit 54.

Audio classification unit 40 uses the enhanced audio information from fast beamformer 20 to classify acoustic events such as, for example and without limitation, snoring events. Other acoustic events such as coughing, sneezing, and groaning events may also be classified by the audio classification unit 40. Known sound classification techniques may be employed in the audio classification unit 40 to classify the acoustic events. For example and without limitation, the sound classification techniques described in U.S. Patent Application Publication No. 2011/0087079 can be suitably modified for use in audio classification unit 40. As the enhanced audio information from fast beamformer 20 only includes sounds from directions inside its beam, the enhanced audio information from fast beamformer 20 is relatively noise-free audio of a patient's snoring, and thus the enhanced audio information from fast beamformer 20 is well suited for use in classifying snoring events. Audio classification unit 40 output information of the classified acoustic events.

System 1 also includes head movement detection unit 50 including first head movement detection unit 52 and second head movement detection unit 54. Head movement detection unit 50 detects movement of the patient's head based on the enhanced audio information of slow beamformer 20 and noise information of fast beamformer 20 and slow beamformer 30.

First head movement detection unit 52 receives the enhanced audio information from slow beamformer 30. As described above, slow beamformer 30 does not adapt fast enough to track movement of the patient's head. As such, during periods of snoring and head movement, the enhanced audio information of slow beamformer 30 will change due to its beam not being directly focused on the patient's head. First head detection movement unit 52 analyzes the enhanced audio information of slow beamformer 30 for such changes and thusly determines when head movement occurs. In some exemplary embodiments, first head movement detection unit 52 includes an envelope analysis unit which performs envelope analysis on the enhanced audio information of slow beamformer 30 to determine when head movement occurs. First head movement detection unit 52 output first head movement information.

System 1 further includes second head movement detection unit 54. second head movement detection unit 54 receives noise information from both fast beamformer 20 and slow beamformer 30. As described above with reference to FIGS. 2B and 2C, a difference in noise information between fast beamformer 20 and slow beamformer 30 can indicate a period of head movement. Second head movement detection unit 54 analyzes the noise information from fast beamformer 20 and slow beamformer 30 to determine when head movement occurs. Second head movement detection unit 54 can include, for example and without limitation, a filter analysis unit. Second head movement detection unit 54 outputs second head movement information.

System 1 further includes a diagnosis unit 70. Diagnosis unit 70 receives outputs of audio classification unit 40 head movement detection unit 50. That is, diagnosis unit 70 receives audio classification information from audio classification unit 40, first head movement information from first head movement detection unit 52, and second head movement information from second head movement detection unit 54. From the received information, diagnosis unit 70 is able to analyze snoring and head movement patterns of the patient.

Snoring information alone may not accurately indicate a sleep apnea condition. Likewise, head movement information alone may also not accurately indicate a sleep apnea condition. By utilizing both snoring information and head movement information, diagnosis unit 70 is able to more accurately diagnose a sleep apnea condition. Diagnosis unit 70 outputs information on the diagnosed sleep apnea condition which can then be used to, for example, prescribe a treatment program for the patient.

Furthermore, system 1 can diagnose a sleep apnea condition from only audio of the patient. As such, system 1 is less obtrusive than other sleep apnea diagnosis systems which use sensors such as accelerometers to monitor head movement of the patient. Also, since system 1 uses both snoring information and head movement information, system 1 can provide a more accurate diagnosis than other sleep apnea diagnosis systems which only use snoring event information or only use head movement information.

Figure 3:
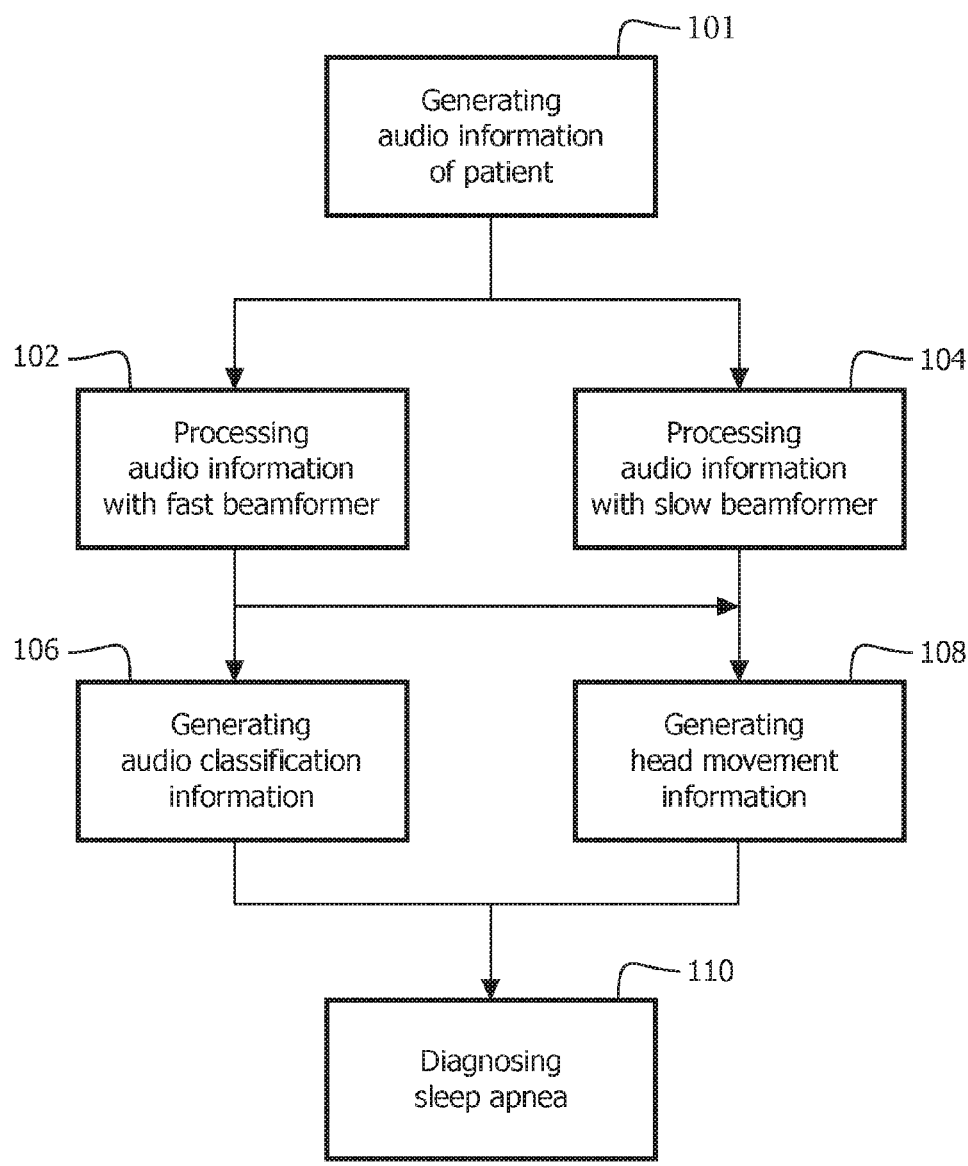
FIG. 3 is a flow chart of a method of generating audio classification information and head movement information according to one exemplary embodiment.

Referring to FIG. 3, a flow chart for a method of generating audio classification and head movement information according to one exemplary embodiment is shown. The audio classification and head movement information can subsequently be used to diagnose sleep apnea. The method begins at step 101 where sounds generated by a patient are detected and audio information of the patient is generated. The detection of sounds generated by the patient and the generation of audio information of the patient can be performed with an array of microphones. The audio information of the patient is then processed with a fast beamformer in step 102 and a slow beamformer in step 104. The fast beamformer has an adaptability speed which is fast enough to track normal head movements of the patient and the slow beamformer has an adaptability speed which is too slow to track normal head movements of the patient, but is fast enough to track normal body movements of the patient. The fast beamformer and slow beamformer each output enhanced audio information and noise information, as described above with respect to FIG. 1.

In step 106, audio classification information is generated. The audio classification information is generated based on the enhanced audio information of the fast beamformer. In step 108, head movement information is generated. The head movement information can include first head movement information generated based on the enhanced audio information of the second beamformer and second head movement information based on the noise information of the fast beamformer and the slow beamformer. As noted above, the audio classification information and the head movement information can subsequently be used to diagnose sleep apnea, as shown in step 110.

The present disclosed concept can be embodied in an electronic apparatus, such as, for example and without limitation, a mobile device, a mobile computer, a tablet computer, a peripheral device etc. The present disclosed concept can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An electronic apparatus comprising:
    an array of microphones for detecting audible sounds generated by a patient and for generating audio information representing the detected audible sounds generated by the patient;
    a first beamformer structured to form a first beam and having a first adaptability speed, wherein the first beamformer is configured to generate first audio information and first noise information from the audio information, wherein the first audio information is comprised of audible sounds from within the first beam and the first noise information is comprised of audible sounds from outside the first beam;
    a second beamformer structured to form a second beam and having a second adaptability speed which is slower than the first adaptability speed, wherein the second adaptive beamformer is configured to generate second audio information and second noise information from the audio information, wherein the second audio information is comprised of audible sounds from within the second beam and the second noise information is comprised of audible sounds from outside second beam;
    an audio classification unit for generating audio classification information based on the first audio information;
    a head movement detection unit for generating head movement information based on changes in the second audio information or differences between the first noise information and the second noise information; and
    a diagnosis unit for determining a sleep apnea diagnosis based on the audio classification information and the head movement information.

2. The electronic apparatus of claim 1, wherein the first adaptability speed is fast enough to track normal head movements of the patient and the second adaptability speed is too slow to track the normal head movements of the patient.

3. The electronic apparatus of claim 1, wherein the first beamformer and the second beamformer are one of filter and sum type beamformers and delay and sum type beamformers.

4. The electronic apparatus of claim 1, wherein the head movement detection unit comprises a first head movement detection unit and a second head movement detection unit and the head movement information comprises first head movement information and second head movement information, wherein the first head movement detection unit is configured to calculate the first head movement information based on the second audio information and the second head movement detection unit is configured to calculate the second head movement information based on the first noise information and the second noise information.

5. The electronic apparatus of claim 4, wherein the first head movement detection unit is an envelope detection unit for calculating the first head movement information based on variations in the second audio information.

6. The electronic apparatus of claim 4, wherein the second head movement detection unit is structured to calculate the second head movement information based on differences between the first noise information and the second noise information.

7. The electronic apparatus of claim 1, wherein the array of microphones are located within about 10 cm or less of each other.

8. A method of diagnoding sleep apnea, the method comprising:
    detecting audible sounds with an array of microphones, wherein the audible sounds are generated by a patient, and generating audio information representing the detected audible sounds generated by the patient;
    processing the audio information with a first beamformer having a first beam and a first adaptability speed and generating first audio information and first noise information from the audio information, wherein the first audible information is comprised of audible sounds from within the first beam and the first noise information is comprised of audible sounds from outside the first beam;
    processing the audio information with a second beamformer having a second beam and a second adaptability speed which is slower than the first adaptability speed and generating second audio information and second noise information from the audio information, wherein the second audio information is comprised of audible sounds from within the second beam and the second noise information is comprised of audible sounds from outside the second beam;

generating audio classification information based on the first audio information;

generating head movement information based on changes in the second audio information or differences between the first noise information and the second noise information; and determining a sleep apnea diagnosis based on the audio classification information and the head movement information.

9. The method of claim 8, wherein the first adaptability speed is fast enough to track normal head movements of the patient and the second adaptability speed is too slow to track the normal head movements of the patient.

10. The method of claim 8, wherein the first beamformer and the second beamformer are one of filter and sum type beamformers and delay and sum type beamformers.

11. The method of claim 8, wherein the generating head movement information comprises generating first head movement information based on the second audio information and generating second head movement information based on the first noise information and the second noise information.

12. The method of claim 11, wherein the generating first head movement information comprises performing envelope analysis on the second audio information to determine variations in the second audio information.

13. The method of claim 11, wherein the generating second head movement information comprises performing filter analysis to determine differences between the first noise information and the second noise information.

14. The method of claim 11, wherein the array of microphones are located within about 10 cm or less of each other.

15. A non-transitory computer readable medium storing one or more programs, including instructions, which when executed by a computer, causes the computer to perform the method as claimed in claim 8.

* * * * *